United States Patent [19]

Fernandez Fernandez et al.

[11] Patent Number: 5,021,449
[45] Date of Patent: Jun. 4, 1991

[54] ORGANIC COMPOUNDS AND THEIR USE AS PHARMACEUTICALS

[75] Inventors: Maria I. Fernandez Fernandez, Madrid, Spain; Terrence M. Hotten, Farnborough; David E. Tupper, Reading, both of England

[73] Assignees: Lilly S.A., Alcobendas, Spain; Lilly Industries Limited, Basingstoke, England

[21] Appl. No.: 412,685

[22] Filed: Sep. 26, 1989

[30] Foreign Application Priority Data

Sep. 30, 1988 [GB] United Kingdom ............... 8823040

[51] Int. Cl.$^5$ ............... C07D 403/12; C07D 409/12; A61K 31/38; A61K 31/40
[52] U.S. Cl. .......................... 514/422; 514/444; 548/527
[58] Field of Search ............... 568/527; 514/422, 444

[56] References Cited

U.S. PATENT DOCUMENTS

| | | | |
|---|---|---|---|
| 3,177,252 | 4/1965 | Thominet | 260/559 |
| 3,342,826 | 9/1967 | Miller et al. | 260/294 |
| 3,932,503 | 1/1976 | Weber et al. | 260/553 DA |
| 4,123,550 | 10/1978 | Untch et al. | 424/275 |
| 4,221,815 | 9/1980 | Weyer et al. | 424/319 |
| 4,321,378 | 3/1982 | Dostert et al. | 544/321 |
| 4,560,751 | 12/1985 | Seybold | 544/60 |
| 4,767,757 | 4/1988 | Daum et al. | 514/354 |
| 4,839,381 | 6/1989 | Daum et al. | 514/444 |
| 4,904,686 | 2/1990 | Fernandez et al. | 514/422 |

FOREIGN PATENT DOCUMENTS

| | | |
|---|---|---|
| 14507 | 10/1988 | Australia . |
| 60235 | 9/1982 | European Pat. Off. . |
| 65295 | 11/1982 | European Pat. Off. . |
| 297697 | 1/1989 | European Pat. Off. . |
| 1937759 | 9/1970 | Fed. Rep. of Germany . |
| 63-267778 | 11/1988 | Japan . |

OTHER PUBLICATIONS

Consiglio, et al., *J. Chem. Soc. Perkin Trans. II*, 1983, 1559-61.
C.A. 72, 3226a (1970).
C.A. 67, 21674w (1967).
C.A. 101, 122562j (1984).
C.A. 100, 84964m (1984).

*Primary Examiner*—Jane T. Fan
*Assistant Examiner*—Celia Chang
*Attorney, Agent, or Firm*—Robert A. Conrad; Leroy Whitaker

[57] ABSTRACT

A pharmaceutical compound of the formula

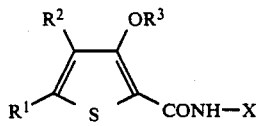

in which $R^1$ is —CHO, $CH_2OH$, —$CH_2OC_{1-4}$ alkyl, —$COC_{1-3}$ alkyl, —$CH(OH)C_{1-3}$ alkyl or —COOH, $R^2$ is $C_{1-4}$ alkyl, —CHO, —$CH_2OH$, —$CH_2OC_{1-4}$ alkyl, —$COC_{1-3}$ alkyl, —$CH(OH)C_{1-3}$ alkyl or —COOH, $R^3$ is $C_{1-4}$ alkyl and X is pyrrolidinyl or pyrrolidinylmethyl; and salts and esters thereof.

5 Claims, No Drawings

ORGANIC COMPOUNDS AND THEIR USE AS PHARMACEUTICALS

This invention relates to organic compounds, their preparation and use as pharmaceuticals.

The compounds of the invention are of the formula

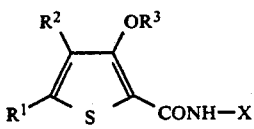 (I)

in which $R^1$ is —CHO, —CH$_2$OH, —CH$_2$OC$_{1-4}$ alkyl, —COC$_{1-3}$ alkyl, —CH(OH)C$_{1-3}$ alkyl or —COOH, $R^2$ is C$_{1-4}$ alkyl, —CHO, —CH$_2$OH, —CH$_2$OC$_{1-4}$ alkyl, —COC$_{1-3}$ alkyl, —CH(OH)C$_{1-3}$ alkyl or —COOH, $R^3$ is C$_{1-4}$ alkyl and X is pyrrolidinyl or pyrrolidinylmethyl; and salts and esters thereof.

The compounds of the invention and their pharmaceutically-acceptable salts and esters have useful effects on the central nervous system and the invention comprises a compound of formula (I) for use as a pharmaceutical and, more particularly, a compound of formula (I) in pharmaceutically-acceptable form.

When X is pyrrolidinyl it is preferably an N-substituted group of the formula

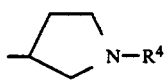

where $R^4$ is C$_{1-4}$ alkyl, C$_{2-4}$ alkenyl or optionally substituted C$_6$H$_5$CH$_2$—. When X is pyrrolidinylmethyl, it is preferably an N-substituted group of the formula

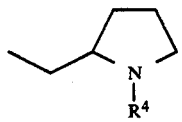

where $R^4$ is C$_{1-4}$ alkyl, C$_{2-4}$ alkenyl or optionally substituted C$_6$H$_5$CH$_2$—. $R^4$ is preferably C$_{1-4}$ alkyl and especially ethyl.

When reference is made to C$_{1-4}$ alkyl this includes, for example, methyl, ethyl, propyl, isopropyl and butyl. A C$_{2-4}$ alkenyl group is preferably vinyl or propenyl. An optionally substituted phenyl is preferably phenyl or a phenyl nucleus substituted with one or more, preferably one to three, substituents selected, for example, from halogen, C$_{1-4}$ alkyl, C$_{1-4}$ alkoxy, hydroxy, nitro, cyano, amino, carboxy and carboxamido.

A preferred group of compounds is of the formula

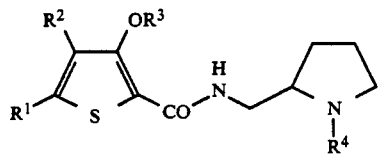

in which $R^1$ is —CHO, —CH$_2$OH or —COOH, $R^2$ is methyl, —CHO, —CH$_2$OH or —COOH, $R^3$ is C$_{1-4}$ alkyl and $R^4$ is ethyl; and salts and esters thereof.

The novel compounds of the invention are useful both as the free compound or as salts, for example the pharmaceutically-acceptable acid addition salts such as salts derived from non-toxic inorganic acids, for example, hydrochloric acid, nitric acid, phosphoric acid, sulphuric acid, hydrobromic acid, hydriodic acid and phosphorous acid, as well as salts derived from non-toxic organic acids such as aliphatic mono and dicarboxylic acids, especially fumaric acid, phenyl-substituted alkanoic acids, hydroxyalkanoic and hydroxyalkandioic acids, aromatic acids, aliphatic and aromatic sulphonic acids. In addition to pharmaceutically-acceptable salts, other salts are included such as for example, those with picric or oxalic acids; they may serve as intermediates in the purification of the compounds or in the preparation of other, for example pharmaceutically-acceptable, acid addition salts, or are useful for identification, characterisation or purification of the bases.

Acid groups, such as —COOH on the thiophene nucleus, allow the formation of salts with bases. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred. It is preferred that the salt is pharmaceutically-acceptable but, as explained above, other salts are also included in the invention. With regard to esters, these may be formed at the carboxyl group by conventional alcohols. Examples of such alcohols include alkanols of formula $R^4$OH where $R^4$ is alkyl, preferably C$_{1-8}$ alkyl and especially methanol and ethanol. Thus the most preferred ester derivatives are the methyl and ethyl esters of the compounds of formula (I).

It will be appreciated that the compounds of the invention can contain one or more assymetric carbon atom which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form. Such pure forms can be separated from the racemic mixture, or, alternatively, the enantiomers can be prepared by utilising optically active amines in the preparation of the compounds. The preferred enantiomer is the laevorotatory (—) form.

The invention also includes a process for producing a compound according to formula (I) above, which comprises (a) oxidizing a compound of formula (I) in which $R^1$ or $R^2$ is C$_{1-4}$ alkyl, —CHO or —CH$_2$OH, (b) reducing a compound of formula (I) in which $R^1$ or $R^2$ is —CHO or —COC$_{1-3}$ alkyl, (c) reacting a compound of formula (I) in which one or more of $R^1$ and $R^2$ is —CH$_2$OH, with an alkylating agent, or (d) reacting a compound of the formula

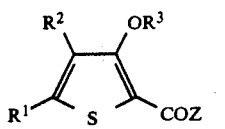

(II)

in which $R^1$, $R^2$ and $R^3$ have the values defined in formula (I), a —COOH being suitably protected by an ester group, and Z is halo, —OH or —OR where R is a leaving group such as $C_{1-4}$ alkyl, with an amine of the formula

XNH$_2$                           (III)

in which X has the values defined in formula (I), optionally followed by the removal of an ester group.

The oxidising step (a), referred to above, is preferably carried out in a suitable solvent such as for example aqueous sulphuric acid and at a temperature of from −20° C. to 60° C., more preferably from 0° C. to 25° C. Examples of oxidising agents that can be employed include $Ce^{IV}$ oxidising agents such as for example cerium ammonium nitrate and cerium sulphate. The reaction can be monitored by means of chromatography in order to detect the formation of the desired product. For instance it may be desired to obtain a product in which one or other of the groups $R^1$ and $R^2$ is not fully oxidised, and to isolate, for example, a compound with $R^1$ or $R^2$ as —CHO.

With regard to the reducing step (b), this is preferably carried out in a suitable solvent such as for example ethanol, and at a temperature of from −20° C. to 60° C., more preferably from 0° C. to 25° C. Examples of suitable reducing agents for this reaction include sodium borohydride or lithium aluminium hydride. As in the case of the oxidising reaction it may be necessary to monitor progress of the reaction to determine when the desired product is obtained. For example it may be desired to prepare a compound in which only one of the $R^1$ and $R^2$ groups is fully reduced. This can be achieved by carefully adjusting the quantity of reducing agent.

The alkylation reaction (c), referred to above, is a conventional step carried out under the usual reaction conditions. For example the reaction is preferably carried out at a temperature of from 0° C. to 100° C. using as alkylating agent an alkyl iodide, and in the presence of a base such as for example sodium hydroxide. Alternatively a trialkyloxonium tetrafluoroborate has been found useful.

With regard to reaction (d) above, it is preferably carried out at a temperature of from 0° C. to 200° C. in an inert organic solvent such as, for example a haloalkane, for example, dichloromethane. When Z is —OH a coupling agent is preferably employed such as a coupling agent commonly used in peptide synthesis, for example carbonyldiimidazole. When Z is OR, it is often desirable to carry out the reaction at a higher temperature, for example from 100° C. to 200° C. The preferred reactions are those in which the reactant is one of formula (II) in which Z is halo or —OH.

One starting point for synthesis of the compounds of the invention are compounds of formula (I) in which both of the $R^1$ and $R^2$ groups are $C_{1-4}$ alkyl. Such compounds can be prepared by a route similar to the condensation reaction described in (d) above, from known amines and 2-carboxylthiophenes synthesised by conventional methods.

Alternatively, intermediates of formula (II) can be synthesised according to literature methods such as described in Ber. 43 901-906 and Ber. 45 2413-2418.

As mentioned above, the compounds of the invention in free base and pharmaceutically-acceptable salt and ester form have useful central nervous system activity. They are also of low toxicity. Their activity has been demonstrated by testing in animal models using well-established procedures. More specifically, the compounds have been shown to block apomorphine induced climbing in mice according to the method of Costall, Naylor and Nohria (European J. Pharmacol. 50, 39; 1978), and/or to block a conditioned avoidance response in rats according to the method of Jacobsen and Sonne (Acta Pharmacol. et Toxacol. 11, 35; 1955), at doses below 50 mg/kg when administered intraperitoneally.

These tests show that the compounds of the invention block post-synaptic dopamine receptors and are accordingly indicated for the treatment of emesis, depression, anxiety and psychotic conditions such as schizophrenia and acute mania.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutically-acceptable salts and esters of the invention will normally be administered orally or by injection and, for this purpose, said compounds will usually be utilised in the form of a pharmaceutical composition. Such compositions are prepared in a manner well known in the pharmaceutical art and normally comprise at least one active compound or pharmaceutically-acceptable salt associated with a pharmaceutically-acceptable diluent or carrier therefor. Such compositions form part of the present invention. In making such compositions, the active ingredient will usually be mixed with a carrier or diluent. Additionally or alternatively it may be enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phosphate, alginates, tragacanth, gelatin, syrup, methyl cellulose, methyl and propylhydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use or injectable solutions for parenteral use. Preferably the compositions are formulated in a dosage unit form, each dosage containing from 1 to 200 mg more usually 5 to 100 mg, of the active ingredient.

The invention is illustrated by the following Preparations and Examples.

PREPARATION 1

Methyl 4,5-dimethyl-3-hydroxythiophene-2-carboxylate

Dry hydrogen chloride gas was bubbled through a mixture of ethyl 2-methyl-3-oxobutanoate (7.6 g, 50 mmol) and methyl 2-mercaptoacetate (11.2 g, 100 mmol) at −10° C. until saturated. The oil was allowed to stand for 3 hours at room temperature, diluted with dichloromethane and washed with brine. After drying with sodium sulphate and evaporation of solvent the oil was dissolved in methanol (10 ml) and added dropwise to methanolic potassium hydroxide (2N; 75 ml), stirring at room temperature for 1 hour. The solution was diluted with iced water (125 ml) and acidified with 3N hydrochloric acid at −3° to 0° C. to pH1. The precipitate was filtered and washed with water (5.5 g, m.p. 50°–51° C., methanol).

PREPARATION 2

Methyl 4,5-dimethyl-3-methoxythiophene-2-carboxylate

To a solution of methyl 3-hydroxy-4,5-dimethylthiophene-2-carboxylate (Preparation 1) (29.7 g, 160 mmol) in anhydrous acetone (500 ml) was added anhydrous potassium carbonte (24.5 g, 178 mmol) and the mixture stirred for 1 hour at room temperature. Dimethyl sulphate (22.4 g, 178 mmol) was added and the mixture stirred under reflux for 2.5 hours. The solvent was evaporated under reduced pressure and the residue partitioned between water and ethyl acetate. The organic phase was washed with brine, dried with sodium sulphate and evaporated to give crude product which was used in the following preparation.

PREPARATION 3

3-Methoxy-4,5-dimethylthiophene-2-carboxylic acid

Methyl 4,5-dimethyl-3-methoxythiophene-2-carboxylate (34 g) was heated under reflux in 1M sodium hydroxide solution (500 ml) for 1 hour. After cooling the mixture was acidified with concentrated hydrochloric acid to pH4. The solid was filtered, washed with water and dried, m.p. 142°–143° C.

PREPARATION 4

Resolution of (±)2-aminomethyl-1-ethylpyrrolidine (+)2-aminomethyl-1-ethylpyrrolidine To a solution of L(+) tartaric acid (80 g) in water (150 ml) was added, dropwise (±)2-aminomethyl-1-ethyl-pyrrolidine keeping the temperature below 20° C. The solution was stirred at room temperature for 1 hour, diluted with ethanol (150 ml) then cooled at 5° C. overnight. The salt was filtered and suspended three times in boiling methanol and filtered whilst warm to give the (+) tartrate (29 g), m.p. 161–162. $(\alpha)_{589}^{25} = +38.8°$ (5% water).

To the above tartrate (29 g) in water (45 ml) was added 30% sodium hydroxide solution (24 ml) and sodium hydroxide pellets (4.5 g), keeping the temperature below 20° C. The solution was extracted with 3×50 ml chloroform. Drying and evaporation of the solvent gave an oil which was distilled $b_{15} \sim 60°$ (6.4 g) $(\alpha)^{25}_{589} = +90°$ (5% chloroform).

(−)-Aminomethyl-1-ethylpyrrolidine was similarly prepared using D(−) tartaric acid as resolving agent. $b_{15} \sim 62°$ (9.4 g) $(\alpha)_{589}^{25} = -151°$ (50% chloroform).

PREPARATION 5

(±) N-[(1-Ethyl-2-pyrrolidinyl)methyl]-3-methoxy-4,5-dimethylthiophene-2-carboxamide, fumarate To a solution of 3-methoxy-4,5-dimethylthiophene-2-carboxylic acid (18.6 g, 0.1 mol) in dry dichloromethane (250 ml) under nitrogen was added 1,1′-carbonyldiimidazole (16.2 g), 0.1 mol). After stirring for 1 hour (±)2-aminomethyl-1-ethylpyrrolidine (12.8 g, 0.1 mol) was added and the solution stirred at room temperature for 24 hours. The reaction mixture was washed successively with 3×40 ml 3M hydrochloric acid, saturated sodium bicarbonate solution and brine. After drying (sodium sulphate) and evaporation of the solvent the residual oil was dissolved in hot ethyl acetate (750 ml), and fumaric acid (9.3 g) added. The fumarate salt was crystallised from the cooled solution and was filtered, m.p. 123°–125° C.

PREPARATION 6

(±) N-[(1-Ethyl-2-pyrrolidinyl)methyl]-3-methoxy-4,5-dimethylthiophene-2-carboxamide, fumarate To a suspension of 3-methoxy-4,5-dimethylthiophene-2-carboxylic acid (1.86 g, 0.010 mol) in dry toluene (30 ml) and two drops of dimethylformamide, thionyl chloride (1.2 g), 0.010 mol) was added drop-wise. The solution was stirred for 15 minutes, the solvent evaporated under vacuum, and a solid was obtained. To a solution of this solid in dry dichloromethane (50 ml) under a nitrogen atmosphere (±) 2-aminomethyl-1-ethylpyrrolidine (1.28 g, 0.010 mol) was added. The solution was stirred for 3 hours, the mixture was partitioned between diluted hydrochloric acid and dichloromethane.

The organic layer was washed with sodium bicarbonate solution and brine, dried with sodium sulphate and evaporated. The residue was dissolved in boiling ethylacetate and fumaric acid (0.088 mol) added. After crystallisation, the solid was filtered, m.p. 121°–123° C.

EXAMPLE 1

(±) N-[(1-Ethyl-2-pyrrolidinyl)methyl]-5-formyl-3-methoxy-4-methylthiophene-2-carboxamide To a solution of (±) N-[(1-ethyl-2-pyrrolidinyl)methyl]-3-methoxy-4,5-dimethylthiophene-2-carboxamide, fumarate (3 g) in dilute sulphuric acid (100 ml concentrated sulphuric acid in 500 ml water) was added ammonium cerium nitrate (17.56 g) in one portion. After stirring at room temperature for 0.5 hours and then cooling to 0° C., 0.88 ammonia solution (235 ml) was added dropwise to give a neutral solution. This was extracted several times with dichloromethane, the organic extracts combined and washed with water, dried over magnesium sulphate and the solvent removed in vacuo to give a light brown oil. Column chromatography on silica eluting with 10% methanol in dichloromethane gave the pure free base of the title compound, fumarate salt, m.p. 122°–123° C. (ex ethyl acetate-ethanol as recrystallising solvent).

EXAMPLE 2

(±)
N-[(1-Ethyl-2-pyrrolidinyl)methyl]-5-hydroxymethyl-3-methoxy-4-methylthiophene-2-carboxamide To a solution of (±) N-[(1-ethyl-2-pyrrolidinyl)methyl]-5-formyl-3-methoxy-4-methylthiophene-2-carboxamide (1.15 g) in ethanol (30 ml) was added sodium borohydride (0.154 g) in one portion. The solution was stirred at room temperature for 2 hours and then water (50 ml) added. After extraction with ethyl acetate, washing the organic extracts with water, drying over magnesium sulphate and filtering, the solvent was removed in vacuo to give the title compound as a golden oil, fumarate salt, m.p. 118°–119° C. (ex ethylacetate-ethanol ether as recrystallising solvent).

EXAMPLE 3

(−)
N-[(1-Ethyl-2-pyrrolidinyl)methyl]-5-formyl-3-methoxy-4-methylthiophene-2-carboxamide The above compound was synthesised from (−) 4,5-dimethyl N-[(1-ethyl-2-pyrrolidinyl)methyl]-3-methoxy thiophene-2-carboxamide in a similar manner outlined in Example 1.

EXAMPLE 4

(−)
N-[(1-Ethyl-2-pyrrolidinyl)methyl]-5-hydroxymethyl-3-methoxy-4-methylthiophene-2-carboxamide The above compound was synthesised from (−) N-[(1-ethyl-2-pyrrolidinyl)methyl]-5-formyl-3-methoxy-4-methylthiophene-2-carboxamide in a similar manner outlined in Example 2.

PREPARATION 7

Dimethyl 3-hydroxy-4-methyl-2,5-thiophene dicarboxylate

To a solution of sodium methoxide from sodium (5.4 g) in methanol (100 ml) was added a solution of methyl pyruvate (24 g) and dimethyl thiodiacetate (41.83 g) in methanol (50 ml). The reaction was stirred at room temperature for 2 days, and then added to ice water (500 ml). After neutralization with 5N HCl and extraction with chloroform, the organics were washed with brine, dried over anhydrous magnesium sulphate, filtered and the solvent evaporated to give a solid, m.p 95°–97° ex methanol.

PREPARATION 8

Trimethyl 3-hydroxy-2,4,5-thiophene tricarboxylate

The above compound was prepared as in Preparation 7 from dimethyl ketomalonate and dimethyl thiodiacetate.

PREPARATION 9

Dimethyl 3-methoxy-4-methyl-2,5-thiophene dicarboxylate

A solution of dimethyl 4-hydroxy-3-methyl-2,5-thiophene dicarboxylate (4.26 g) in acetone (100 ml) containing anhydrous potassium carbonate (2.34 g) was stirred for 1 hour at room temperature. Dimethyl sulphate (1.62 ml) was added and the solution refluxed for 2 hours. The solvent was then removed under vacuum and, after treating the residue with water-ethyl acetate, was extracted several times with ethyl acetate; the organic extracts were collected, washed with water, dried over anhydrous magnesium sulphate, filtered and the solvent evaporated to give a solid, m.p. 61°–64° ex methanol.

PREPARATION 10

Trimethyl 3-methoxy-2,4,5-thiophene tricarboxylate

The above compound was prepared as in Preparation 9 from trimethyl 3-hydroxy-2,4,5-thiophene tricarboxylate.

EXAMPLE 5

(±)
5-Carbomethoxy-N-[1-ethyl-2-pyrrolidinylmethyl]-3-methoxy-4-methylthiophene-2-carboxamide The above compound was prepared by heating dimethyl-3-methoxy-4-methyl-2,5-thiophene dicarboxylate and (±)2-(aminomethyl)-1-ethyl-pyrrolidine at 170° under nitrogen atmosphere. After column chromatography, the title compound was obtained, as its fumarate salt, m.p. 155°–156° ex ethyl acetate.

EXAMPLE 6

(±)
4,5-Dicarbomethoxy-N-[1-ethyl-2-pyrrolidinylmethyl]-3-methoxythiophene-2-carboxamide The above compound was prepared from trimethyl 3-methoxy-2,4,5-thiophene tricarboxylate and (±) 2-(aminomethyl)-1-ethyl-pyrrolidine as in Example 5.

EXAMPLE 7

(−)
5-Carbomethoxy-N-[1-ethyl-2-pyrrolidinylmethyl]-3-methoxy-4-methylthiophene

The above compound was prepared from dimethyl 3-methoxy-4-methyl-2,5-thiophene dicarboxylate and (−) 2-(aminomethyl)-1-ethyl-pyrrolidine as in Example 5.

EXAMPLE 8

(−)
4,5-Dicarbomethoxy-N-[1-ethyl-2-pyrrolidinylmethyl]-3-methoxythiophene-2-carboxamide The above compound was prepared from trimethyl 3-methoxy-2,4,5-thiophene carboxylate and (−) 2-(aminomethyl)-1-ethylpyrrolidine as in Example 5.

The following Examples illustrate the preparation of typical formulations containing an active ingredient according to the invention.

EXAMPLE 9

Hard gelatin capsule

Each capsule contains

| Active ingredient | 10 mg |
|---|---|
| PEG 4000 | 250 mg |

The PEG 4000 is melted and mixed with the active ingredient. Whilst still molten the mixture is filled into capsule shells and allowed to cool.

EXAMPLE 10

Tablet

Each tablet contains

| Active ingredient | 10 mg |
|---|---|
| Calcium carbonate | 300 mg |
| Magnesium stearate | 10 mg |
| Starch | 30 mg |
| Hydroxypropylmethyl-cellulose | 10 mg |
| Iron Oxide | 4 mg |

The active ingredient is granulated with calcium carbonate and starch. The dried granulate is blended with lubricant and disintegrant and compressed into tablets of the required dosage strength. The tablet may then be coated.

EXAMPLE 11

Injection

| Active ingredient | 10 mg |
|---|---|
| Water | 1 mg |

The active ingredient is dissolved in water and distributed into vials, ampoules or pre-pack syringes using appropriate equipment. The product is sterilised.

We claim:

1. A compound of the invention of the formula

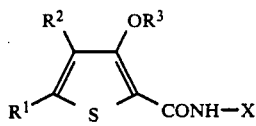

in which $R^1$ is —CHO, —CH$_2$OH, —CH$_2$OC$_{1-4}$ alkyl, —COC$_{1-3}$ alkyl, —CH(OH)C$_{1-3}$ alkyl or —COOH, $R^2$ is C$_{1-4}$ alkyl, —CHO, —CH$_2$OH, —CH$_2$OC$_{1-4}$ alkyl, —COC$_{1-3}$ alkyl, —CH(OH)C$_{1-3}$ alkyl, or —COOH, $R^3$ is C$_{1-4}$ alkyl and X is pyrrolidinyl or pyrrolidinylmethyl; or a salt or an ester of a carboxylic acid thereof.

2. A compound according to claim 1 in which X is a group of formula

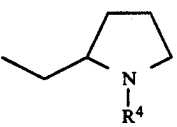

where $R^4$ is C$_{1-4}$ alkyl, C$_{2-4}$ alkenyl, phenyl, or phenyl substituted with one to three substituents selected from halogen, C$_{1-4}$ alkyl, C$_{1-4}$ alkoxy, hydroxy, nitro, cyano, amino, carboxy, and carboxamido.

3. A compound of the formula

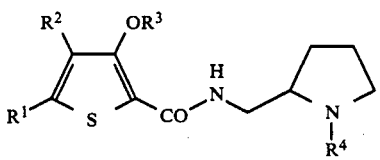

in which $R^1$ is —CHO, —CH$_2$OH or —COOH, $R^2$ is methyl, —CHO, —CH$_2$OH or —COOH, $R^3$ is C$_{1-4}$ alkyl and $R^4$ is ethyl; or a salt thereof.

4. A pharmaceutical formulation comprising effective amount of a central nervous system compound according to claim 1 or a pharmaceutically-acceptable salt or ester thereof, together with a pharmaceutically-acceptable diluent or carrier therefor.

5. A method of treating an animal, or a human, suffering from emesis, depression, anxiety, schizophrenia, or acute mania, which comprises administering an effect amount of a compound according to claim 1 or a pharmaceutically-acceptable salt or ester thereof.

* * * * *